(12) United States Patent
Tani

(10) Patent No.: US 7,638,146 B2
(45) Date of Patent: Dec. 29, 2009

(54) ANTI-AIDS DRUG

(76) Inventor: Michio Tani, 19-18, Jiyugaoka 1-chome, Meguro-ku, Tokyo 152-0035 (JP)

( * ) Notice: Subject to any disclaimer, the term of this patent is extended or adjusted under 35 U.S.C. 154(b) by 64 days.

(21) Appl. No.: 11/993,082

(22) PCT Filed: Jun. 20, 2005

(86) PCT No.: PCT/JP2005/011297

§ 371 (c)(1),
(2), (4) Date: Feb. 1, 2008

(87) PCT Pub. No.: WO2006/137122

PCT Pub. Date: Dec. 28, 2006

(65) Prior Publication Data

US 2008/0199488 A1    Aug. 21, 2008

(51) Int. Cl.
*A01N 65/00* (2009.01)

(52) U.S. Cl. .................................... 424/725

(58) Field of Classification Search ............ None
See application file for complete search history.

(56) References Cited

U.S. PATENT DOCUMENTS

2004/0142000 A1    7/2004 Suga et al.

FOREIGN PATENT DOCUMENTS

| JP | 355058080 | * | 4/1980 |
|----|-----------|---|--------|
| JP | 11-005745 A | | 1/1999 |
| JP | 11-335292 A | | 12/1999 |
| JP | 2004-59558 A | | 2/2004 |
| JP | 2004-210762 A | | 7/2004 |
| WO | 02/087603 A1 | | 11/2002 |

OTHER PUBLICATIONS

Siv, Yeim Yok et al., "Flavonoids from Cambodian Plants Belonging To Genera Cananga, Colonga, Grewia, Leea, and Melastoma", Plantes Medicinales et Phytotherapie, 1972, vol. 6 , No. 4, pp. 299-305.

Lin, Jen-Kun et al., Survey of Catechins, Gallic Acid and Methylxanthines In Green, Oolong, Pu-erh and Black Teas, J. Agric. Food Chem., 1998. vol. 46, No. 9, pp. 3635-3642.

Xu, Hong-Xi et al., "Inhibitory Activity of Flavonoids and Tannins Against HIV-1 Protease", Biol. Pharm. Bull., 2000, vol. 23, No. 9, pp. 1072-1076.

International Search Report of PCT/JP2005/011297 filed Jun. 20, 2005, date of mailing Nov. 13, 2005.

* cited by examiner

*Primary Examiner*—Michael V Meller
(74) *Attorney, Agent, or Firm*—Young & Thompson

(57) ABSTRACT

An anti-AIDS agent which comprises, as the active ingredients, one or more components selected from the group consisting of *Melastoma villosum* Lodd., *Dipterocarpus obtusifolius Teijsm* ex Miq., *Lyophyllum aggregatum, Dictyophora indusiata,* pu-erh tea, *mentha* and *stevia*. Since the foods having been confirmed as safe in practice are employed, this agent is completely safe to take over a long time.

7 Claims, 1 Drawing Sheet

FIG. 1 Change of Concentration Level of HIV Antigen RNA in Blood after Administration of Inventive Anti-AIDS Agent (Average of 24 AIDS Cases)
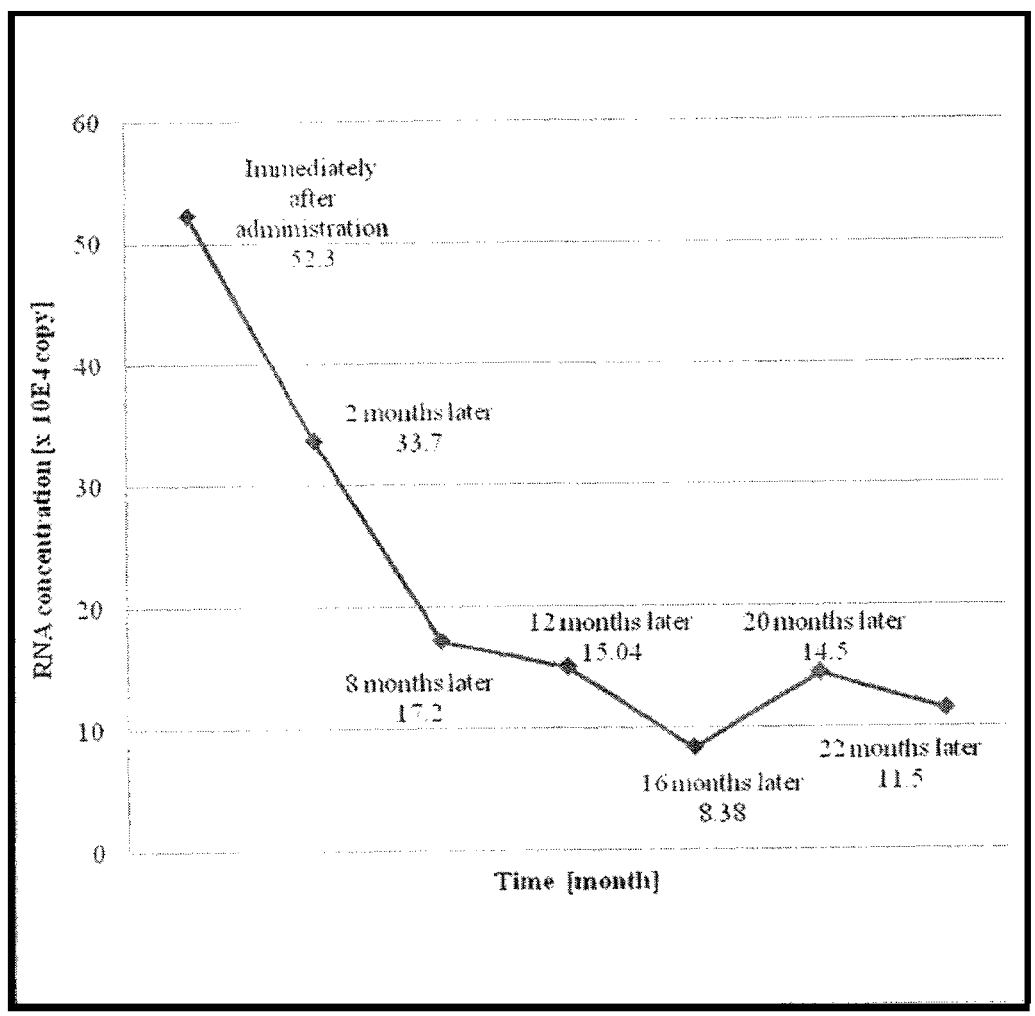

ANTI-AIDS DRUG

TECHNICAL FIELD

The present invention relates to an anti-AIDS agent, and more particularly to an anti-AIDS agent that contains, as the active ingredients, *Melastoma villosum* Lodd., *Dipterocarpus obtusifolius* Teijsm ex Miq., *Lyophyllum aggregatum*, *Dictyophora indusiata*, pu-erh tea, *mentha* and *stevia*.

BACKGROUND ART

AIDS refers to a serious immunodeficiency syndrome caused by infection of a human immunodeficiency virus (HIV) which is an etiologic virus of AIDS. In Japan and China, crude drug and Chinese herbal medicine have been traditionally used for treatment and prevention of diseases from ancient times. Such crude drug and Chinese herbal medicine are typically proved to be of sufficient security, which can, therefore, be taken free of care. Some of them have a remarkable anti-virus effect of suppressing virus propagation. In particular, some crude drugs have been reported which are for use of preventing AIDS virus infection, and of preventing and treating AIDS symptoms.

For example, it is known that an extract of plant body of *stevia*, mainly a stem and a leaf thereof, prevents an HIV virus from adhering to, invading in, and associating with lymphocytes; and that, more particularly, said extract hinders binding of a CD4 molecule of lymphocytes to a gp 120 molecule of an HIV (see, for example, Laid-open Patent Publication No. H11-335292). An anti-HIV activation material is known that is obtained in the following process: preparing an extract of *mentha* by using water, and refining the extract by way of DEAE negative ion exchange chromatography (see, for example, Laid-open Patent Publication No. H11-005745). An AIDS medical drug is known such as one containing catechin or tannin (see, for example, Laid-open Patent Publication No. 2004-210762). It is also known that a *Dictyophora indusiata*-derived ingredient is absorbed in a human body through the mucous membrane to stimulate and activate the mucosal immunity, and that some beneficial effects can thus be expected such as an anti-tumor effect and an effect beneficial for treatment and remedy of infectious diseases caused by virus like AIDS, bacteria or the like (see, for example, WO2002/087603 pamphlet). It is further known that a drug product helps activate the immunization of a patient suffering from a disease like AIDS when the patient has an extremely low activity of the helper T cell, where said drug product is prepared in the method comprising the steps of: dissolving a hydrothermal extract of *Hypsizigus marmoreus* in a lower alcohol solution; removing insoluble matters therefrom; mixing the solution with at least one selected from the group consisting of Okara paste, *chlorella*, *spirulina*, yeast extract, powdered royal extract and powdered propolis; and formulating the mixture into a drug product (see, for example, Laid-open Patent Publication No. 2004-059558). However, what has been desired to be developed is a drug having much more beneficial effect and much less side effect than any one of the above-mentioned therapeutic agents.

And it has not been known that *Melastoma villosum* Lodd., *Dipterocarpus obtusifolius* Teijsm ex Miq. and pu-erh tea have an anti-AIDS effect.

DISCLOSURE OF THE INVENTION

Problem to be Solved by the Invention

Bearing these circumstances in mind, the present invention is intended to provide an anti-AIDS agent which is made of crude drugs available from natural products, and which is thus quite safe and secure for long-term regular use, free from any such serious side effects as can be observed in chemical drugs.

Means for Solving the Problem

This object is achieved by using an anti-AIDS agent containing, as the active ingredients, one or more components selected from the group consisting of *Lyophyllum aggregatum, Dictyophora indusiata*, pu-erh tea, *mentha* and *stevia*.

EFFECTS OF THE INVENTION

The anti-AIDS agent of the present invention exhibits a remarkable anti-AIDS activity through continuous use thereof. Being made of crude drugs and food materials that have traditionally been used safe and secure, the inventive anti-AIDS agent is quite safe and secure, free from any such serious side effects as can be observed in chemical drugs, and the inventive drug can be prepared at a lower cost owing to the easy availability of the raw materials to be used for the preparation. Also, the number of AIDS virus will be reduced by taking the inventive anti-AIDS drug through daily life.

The embodiment of the present invention will be described in detail hereinafter.

BEST MODE FOR CARRYING OUT THE INVENTION

A leaf portion of *Melastoma villosum* Lodd. and a fruit portion of *Dipterocarpus obtusifolius* Teijsm ex Miq. are preferably used for the inventive anti-AIDS agent. In particular, their dried substances have been traditionally used as crude drug throughout the Southeast Asia region including Thailand; hence these two substances do not pose any safety problem. *Lyophyllum aggregatum* (academic name: *Lyophyllum shimeji*), which is an ingredient for the inventive agent, is a type of mushroom classified into *Lyohyllum*, Tricholomataceae. This mushroom grows densely in a copse of quercus serrata, sawtooth oak and the like, and has traditionally been eaten; hence this mushroom does not pose any safety problem. *Dictyophora indusiata* (academic name: *Dictyophora indusiata*), which is an ingredient for the inventive agent, is a type of mushroom classified into *Phallus*. This mushroom grows gregariously or individually on the ground of a bamboo grove, broadleaf forest and the like, and has traditionally been used for Chinese dishes etc.; hence this mushroom does not pose any safety problem. Pu-erh tea, which is an ingredient for the inventive agent, is a type of fermented green tea, the production method thereof comprising fermentation of green tea with *aspergillus* for more than three years. Pu-erh tea is also called black tea in China where said tea has been drunk for more than 1700 years, and hence does not pose any safety problem. *Mentha* (academic name: *Mentha arvensis*), which is an ingredient for the inventive agent, is a perennial plant classified into *Mentha arvensis* var. piperascens, Lamiaceae.

*Mentha*, rich in menthol, has traditionally been applied for fragrance or medicinal use, and hence does not pose any safety problem. *Stevia*, which is an ingredient for the inventive agent, is *Stevia rebaudiana Bertoni*, a perennial plant originated from South America, and classified into Asteraceae. *Stevia* has been generally used as a sweetener etc., and hence does not pose any safety problem.

The anti-AIDS agent of the present invention can also be prepared as a hydrothermal extract of *Melastoma villosum* Lodd., *Dipterocarpus obtusifolius Teijsm* ex Miq., *Lyophyllum aggregatum, Dictyophora indusiata*, pu-erh tea, *mentha* and *stevia*. In this case, these ingredients can be served raw for hydrothermal extraction, but more preferably, they are dried before hydrothermal extraction. Still more preferably, the dried substances are further roasted before hydrothermal extraction. It is also beneficial to spray-dry or freeze-dry the hydrothermal extract solution to be taken as extract powder, granulated powder, tablets or the like. It is still workable that the inventive anti-AIDS agent is taken in the form of dried or roasted fragments, without going through the process of hydrothermal extraction.

Said dried or roasted fragments can be hydrothermally extracted without any pretreatment; but from the practical point of view, further pulverization of the fragments is preferably conducted before extraction. A non-limiting example of weight ratio between hot water used as extraction solvent and said dried or roasted fragments is 10-50:1; more particularly, 20-40:1 in terms of operational efficiency of the extraction. Efficient extraction is expected at high temperature, though somewhat low temperature is also acceptable for sufficient extraction; and in particular, the temperature is preferably within the range of 70 to 100° C. Extraction time is properly determined according to the temperature, such that the active ingredients are successfully extracted. The extraction is implemented under pressurized, non-pressurized or depressurized conditions. More particularly, the preferable extraction condition is at normal pressures, within the temperature range of 85 to 100° C., the extraction time being between 30 and 60 minutes.

In regard to the roasting method, *Melastoma villosum* Lodd., *Dipterocarpus obtusifolius Teijsm* ex Miq., *Lyophyllum aggregatum, Dictyophora indusiata*, pu-erh tea, *mentha* and *stevia*, each being dried, can be roasted without any pretreatment; but it is preferred, from the practical point of view, that they are coarsely pulverized before being roasted. For coarse pulverization of said dried substances, conventional methods are applied using a crusher etc. to create particles of between 0.2 and 2.0 mm in size. Examples of said conventional method include sand roasting, wire mesh roasting, hot-air roasting and microwave oven roasting. Roasting conditions such as roasting time and temperature are properly determined according to the amount of the mixture to be roasted at one time. For example, in case of roasting 100 g of the mixture, the preferable temperature is 110-130° C. and the preferable time is 10-18 minutes.

The dry weight ratio of all of said ingredients to be blended in the inventive anti-AIDS agent, namely, *Melastoma villosum* Lodd., *Dipterocarpus obtusifolius Teijsm* ex Miq., *Lyophyllum aggregatum, Dictyophora indusiata*, pu-erh tea, *mentha* and *stevia*, is preferably 2-5:2-5:1-4:1-4:1-4:0.5-2: 0.5-2; and more preferably, 3:3:2:2:2:1:1.

Non-limiting examples of administration methods of the inventive anti-AIDS agent, including oral and parenteral administrations, comprise rectal administration, nasal administration, buccal administration, sublingual administration, vaginal administration, intramuscular administration, subcutaneous administration and intravenous administration. An oral administration is the most preferable for the inventive agent. Besides, the formulation of the inventive anti-AIDS agent can be properly selected depending on the administration route and so on. Examples of formulation suitable for oral administration include tablets, capsules, powdered formulation, subtle granules, granular formulation, liquid formulation and syrup formulation. Examples of formulation suitable for parenteral administration include injectable solution, intravenous fluids, suppository, inhaler, transdermal formulation, transmucosal formulation and adhesive formulation. Said injectable solution may contain any one of the formulations for intravenous injection, intramuscular injection, subcutaneous injection and intravenous instillation; in particular, the most preferable one is the oral formulation.

The anti-AIDS agent of the present invention may, according to the necessity, further contain such additives as are permissible in terms of pharmacology and galenical pharmacy. Examples of said additives may include fillers, disintegrants/disintegration aids, binder, lubricant, coating agent, pigment, diluents, base material, dissolving agent/dissolving aids, tonicity agent, pH regulator, stabilizing agent, propellant, adhesive and moistening agent. Combination of these additives according to the usage will provide the inventive anti-AIDS agent with a variety of additional effects. For example, a configuration of the anti-AIDS agent can, where appropriate, be designed such that anti-AIDS active substances will be sustainedly released. Another configuration can be designed such that the anti-AIDS active substances will be intensively released at a targeted portion of a human body at which application of the substances is required. Such sustained release preparation and drug delivery system can be designed and produced according to the method well-known to those skilled in the art in the drug formulation industry.

The inventive anti-AIDS agent may contain organic or inorganic carriers. Examples of said carriers include lactose, amylum, vegetable and animal fat and fatty oil.

A dose of the inventive anti-AIDS agent can be properly determined in consideration of a variety of conditions such as the purpose of treatment or preventative care; the patient's sex, weight and age; the type and extent of the disease; drug formulation; administration route and number of doses. In the case of oral administration, the suitable dosage amount a day is 9-30 g of the dried mixture, which is to be taken either after hydrothermal extraction, or after roasting and then hydrothermal extraction. Where the hydrothermal extract solution is spray-dried or freeze-dried to be taken as extract powder, granules, tablets or the like, the suitable dosage amount is 4.0-7.0 g of the dried mixture.

Next, the inventive anti-AIDS agent can be blended in common foods including soups, beverages (juice, sake, mineral water, coffee, tea etc.), confectionaries (gum, candy, chocolate, snack, jelly etc.), noodles (soba, udon, ramen etc.); health food products and dietary supplements (nutritious drink etc.). This will allow for comfortable daily consumption of the inventive anti-AIDS agent.

Also, the concentration level of the inventive anti-AIDS agent in food or beverage can be changed depending on the type of the food or beverage; the preferable daily consumption amount of the extract powder, prepared through spray-drying and freeze-drying the hydrothermal extract solution, is 2.0-12.0 g, and more preferably, 4.0-7.0 g. Said concentration level is a non-limiting example that can be properly changed depending on a variety of circumstances.

EXAMPLES

The present invention is further described with reference to the following examples, which should not be construed to limit the scope of the invention.

Example 1

Preparation of Anti-AIDS Agent 3.0 g of dried *Melastoma villosum* Lodd., 3.0 g of dried *Dipterocarpus obtusifolius Teijsm ex Miq.*, 2.0 g of dried *Lyophyllum aggregatum*, 2.0 g of dried *Dictyophora indusiata*, 2.0 g of dried pu-erh tea, 1.0 g of dried *mentha* and 1.0 g of dried *stevia* were mixed, coarsely pulverized, and roasted at 115° C. for 16 minutes to prepare the anti-AIDS agent of the present invention.

Example 2

Preparation of Anti-AIDS Agent 3.0 of dried *Melastoma villosum* Lodd., 3.0 g of dried *Dipterocarpus obtusifolius Teijsm ex Miq.*, 2.0 g of dried *Lyophyllum aggregatum,* 2.0 g of dried *Dictyophora indusiata,* 2.0 g of dried pu-erh tea, 1.0 g of dried *mentha* and 1.0 g of dried *stevia* were mixed and coarsely pulverized to prepare the anti-AIDS agent of the present invention.

Experimental Example 1

Clinical trial for measuring the anti-AIDS effect of the present invention was conducted as described below.

The inventive anti-AIDS agent was provided for 24 AIDS cases to be taken twice a day, said agent having been extracted in hot water of 90-100° C. for 40 minutes. Periodical blood drawings were carried out during the intake period to measure the concentration level of HIV antigen RNA. The result is shown in FIG. 1.

It is apparent from FIG. 1 that the concentration level of HIV antigen RNA significantly decreased after dosing the present invention. The result shows that the present invention clearly has the effect of reducing the number of AIDS virus. Therefore, it is proved that the present invention is quite effective as an anti-AIDS agent.

BRIEF DESCRIPTION OF THE DRAWINGS

FIG. 1 is a graph showing the average concentration level of HIV antigen RNA in the blood of 24 AIDS patients continuously taking the anti-AIDS agent of the present invention.

The invention claimed is:

1. A composition comprising *Melastoma villosum* Lodd., *Dipterocarpus obtusifolius Teijsm ex Miq., Lyophyllum aggregatum, Dictyophora indusiata*, pu-erh tea, *mentha* and *stevia*, in a dry weight ratio of 2-5: 2-5: 1-4: 1-4: 1-4: 0.5-2: 0.5-2, respectively.

2. The composition according to claim 1, wherein at least one of *Melastoma villosum* Lodd., *Dipterocarpus obtusifolius Teijsm* ex Miq., *Lyophyllum aggregatum, Dictyophora indusiata*, pu-erh tea, *mentha* or *stevia* is dried.

3. The composition according to claim 1, wherein at least one of *Melastoma villosum* Lodd., *Dipterocarpus obtusifolius Teijsm* ex Miq., *Lyophyllum aggregatum, Dictyophora indusiata*, pu-erh tea, *mentha* or *stevia* is further roasted.

4. The composition according to claim 1, wherein the dry weight ratio is 3: 3: 2: 2: 2: 1: 1, respectively.

5. The composition according to claim 2, wherein the at least one of *Melastoma villosum* Lodd., *Dipterocarpus obtusifolius Teijsm* ex Miq., *Lyophyllum aggregatum, Dictyophora indusiata*, pu-erh tea, *mentha* or *stevia* is further roasted.

6. The composition according to claim 2, wherein the dry weight ratio is 3: 3: 2: 2: 2: 1: 1, respectively.

7. The composition according to claim 3, wherein the dry weight ratio is 3: 3: 2: 2: 2: 1: 1, respectively.

* * * * *